(12) United States Patent
Lawrence et al.

(10) Patent No.: US 6,833,274 B2
(45) Date of Patent: Dec. 21, 2004

(54) CORTISOL SENSOR

(75) Inventors: David S. Lawrence, Olney, MD (US); Jennifer L. Sample, Bethesda, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/441,370

(22) Filed: May 20, 2003

(65) Prior Publication Data

US 2003/0224526 A1 Dec. 4, 2003

Related U.S. Application Data

(60) Provisional application No. 60/383,543, filed on May 28, 2002.

(51) Int. Cl.[7] .......... G01N 33/00; G01N 33/48; G01N 21/76
(52) U.S. Cl. ........... 436/128; 436/164; 436/172; 422/68.1; 422/82.05; 422/82.08
(58) Field of Search .......... 436/128, 164, 436/165, 172; 552/577; 422/68.1, 82.05, 82.08

(56) References Cited

U.S. PATENT DOCUMENTS

| | | | |
|---|---|---|---|
| 5,372,719 A | 12/1994 | Afeyan | |
| 5,453,199 A | 9/1995 | Afeyan | |
| 5,641,539 A | 6/1997 | Afeyan | |
| 5,821,311 A | 10/1998 | Mosbach | |
| 5,858,296 A | * 1/1999 | Domb | 264/330 |
| 5,872,198 A | 2/1999 | Mosbach | |
| 5,959,050 A | 9/1999 | Mosbach | |
| 5,994,110 A | 11/1999 | Mosbach | |
| 6,051,372 A | 4/2000 | Bayerl | |
| 6,127,154 A | 10/2000 | Mosbach | |
| 6,177,513 B1 | * 1/2001 | Takeuchi et al. | 525/54.1 |
| 6,212,959 B1 | * 4/2001 | Perkins | 73/861.77 |
| 6,255,461 B1 | * 7/2001 | Mosbach et al. | 530/389.2 |
| 6,458,599 B1 | 10/2002 | Huang | |
| 2002/0090664 A1 | * 7/2002 | Wiegand et al. | 435/7.92 |
| 2002/0092858 A1 | * 7/2002 | Bowman | 220/709 |
| 2003/0129092 A1 | * 7/2003 | Murray | 422/82.07 |

FOREIGN PATENT DOCUMENTS

| | | | |
|---|---|---|---|
| JP | 11019076 A | | 7/1997 |
| JP | 11023579 A | | 7/1997 |
| JP | 11038004 A | | 7/1997 |
| JP | 11326318 A | | 5/1998 |
| JP | 2000275248 | | 6/2000 |
| WO | 01/77672 | * | 1/2001 |
| WO | 01/86263 | * | 11/2001 |

OTHER PUBLICATIONS

Baggiani et al. Talanta, vol. 51, 2000, pp. 71–75.*

Sreenivasan et al. Journal of Applied Polymer Science, vol. 71, 1999, pp. 1823–1826.*

Kriz et al. Analytical Chemistry, vol. 67, 1995, pp. 2142–2144.*

(List continued on next page.)

*Primary Examiner*—Maureen M. Wallenhorst
(74) *Attorney, Agent, or Firm*—Francis A. Cooch

(57) ABSTRACT

Devices and methods for sensing and detecting cortisol levels in a fluid sample in real-time using a cortisol-imprinted polymer are provided. Also provided are hydration devices that include a cortisol sensor of the present invention capable both of providing hydration to a user and allowing the user to measure cortisol levels in the user's bodily fluids in real-time.

22 Claims, 8 Drawing Sheets

OTHER PUBLICATIONS

Sreenivasan. Journal of Applied Polymer Science, vol. 82, 2001, pp. 889–893.*

Sreenivasan. Journal of Polymer Research, vol. 8, No. 3, Sep. 2001, pp. 197–200.*

Cameron Alexander, Craig R. Smith, Michael J. Whitcombe, and Evgeny N. Vulfson, "Imprinted Polymers as Protecting Groups for Regioselective Modification of Polyfunctional Substrates", J. Am. Chem. Soc. 1999, 121, 6640–6651. [Contains chemistry and schematic for steroid–selective MIP.].

Akimitsu Kugimiya, Toshifumi Takeuchi, "Surface Plasmon Resonance Sensor Using Molecularly Imprinted Polymer for Detection of Sialic Acid" Biosensors & Bioelectronics 16 (2001) 1059–1062.

Jun Matsui, Miho Higashi, and Toshifumi Takeuchi, "Molecularly Imprinted Polymer as 9–Ethyladenine Receptor Having a Porphyrin–Based Recognition Center" J. Am. Chem. Soc. 2000, 122,5128–5219.

* cited by examiner

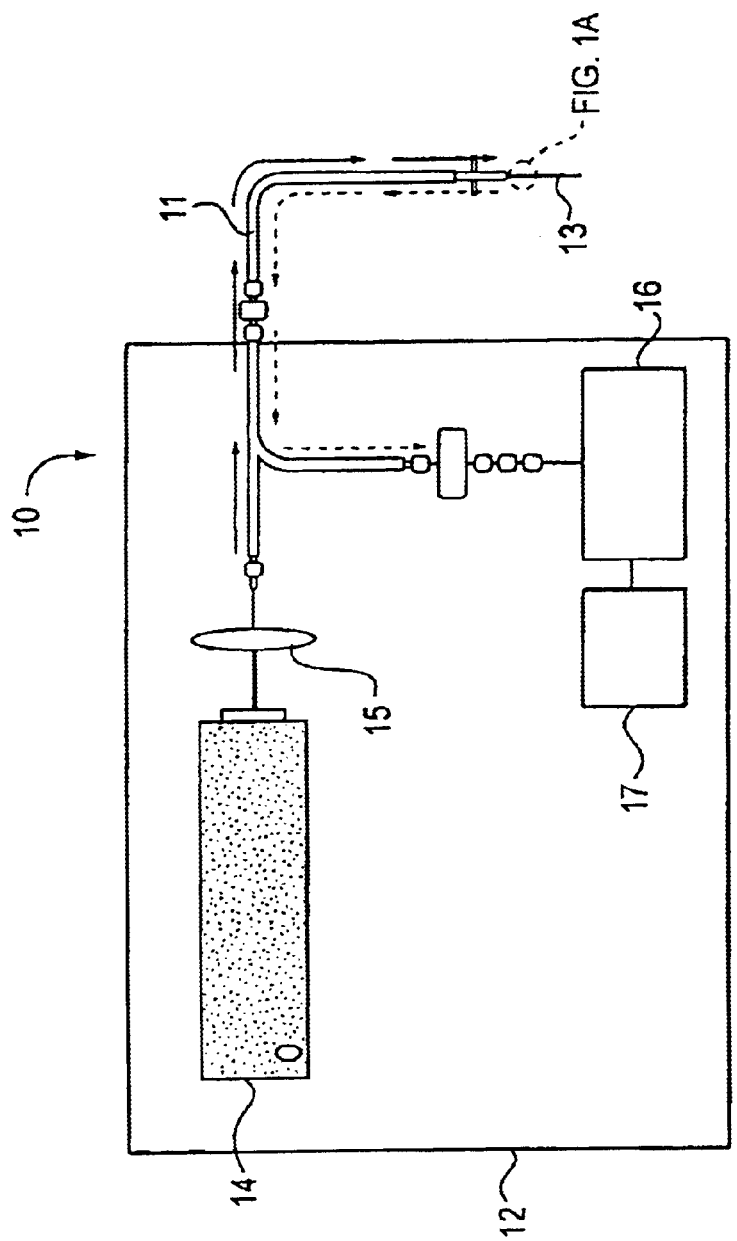
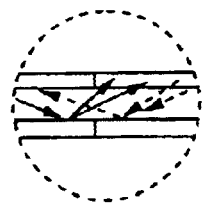
FIG. 1
FIG. 1A

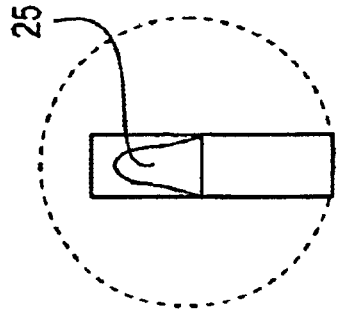
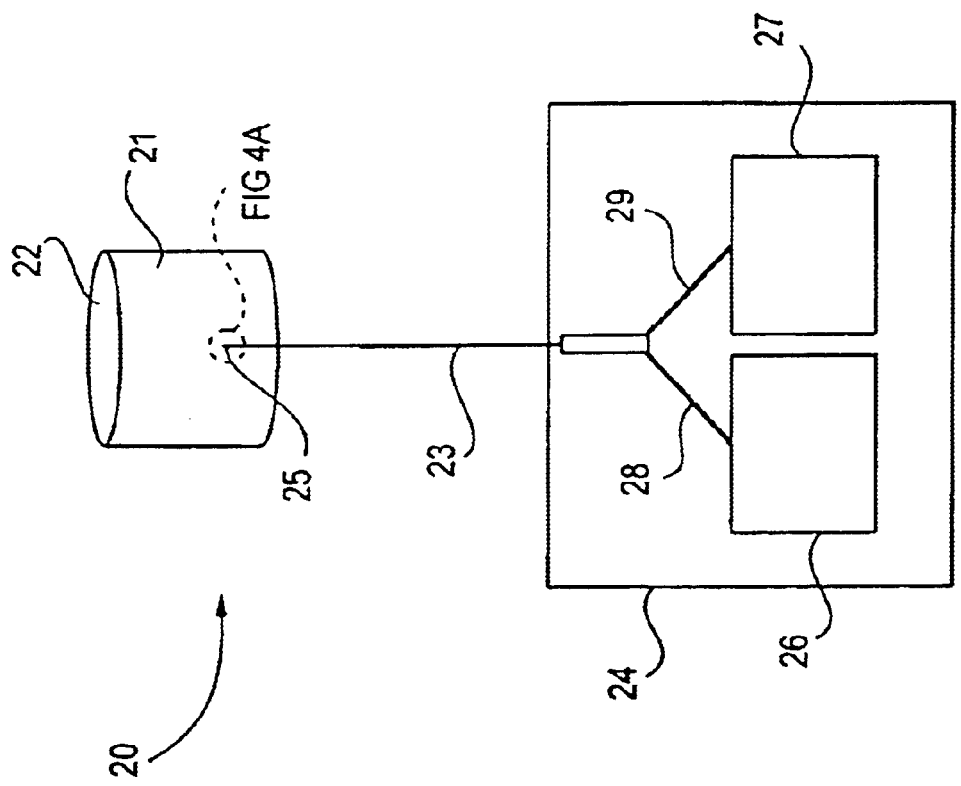

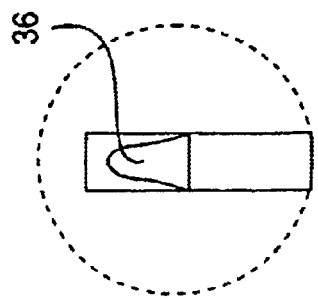
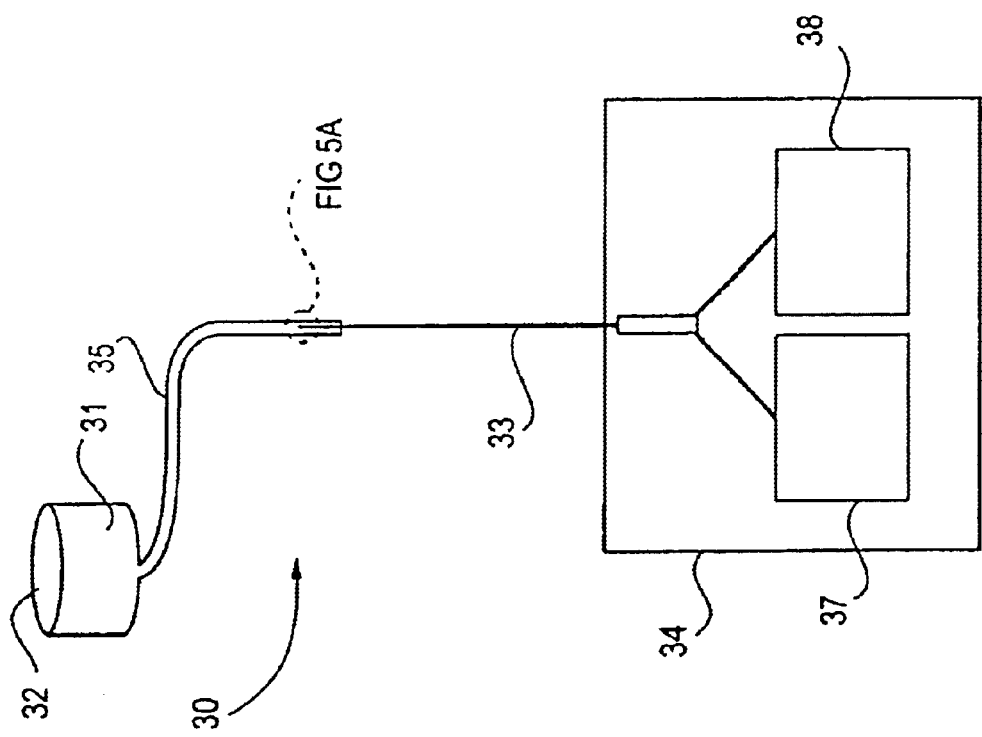

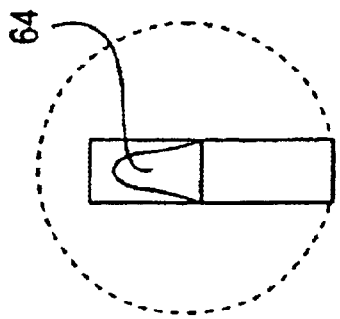
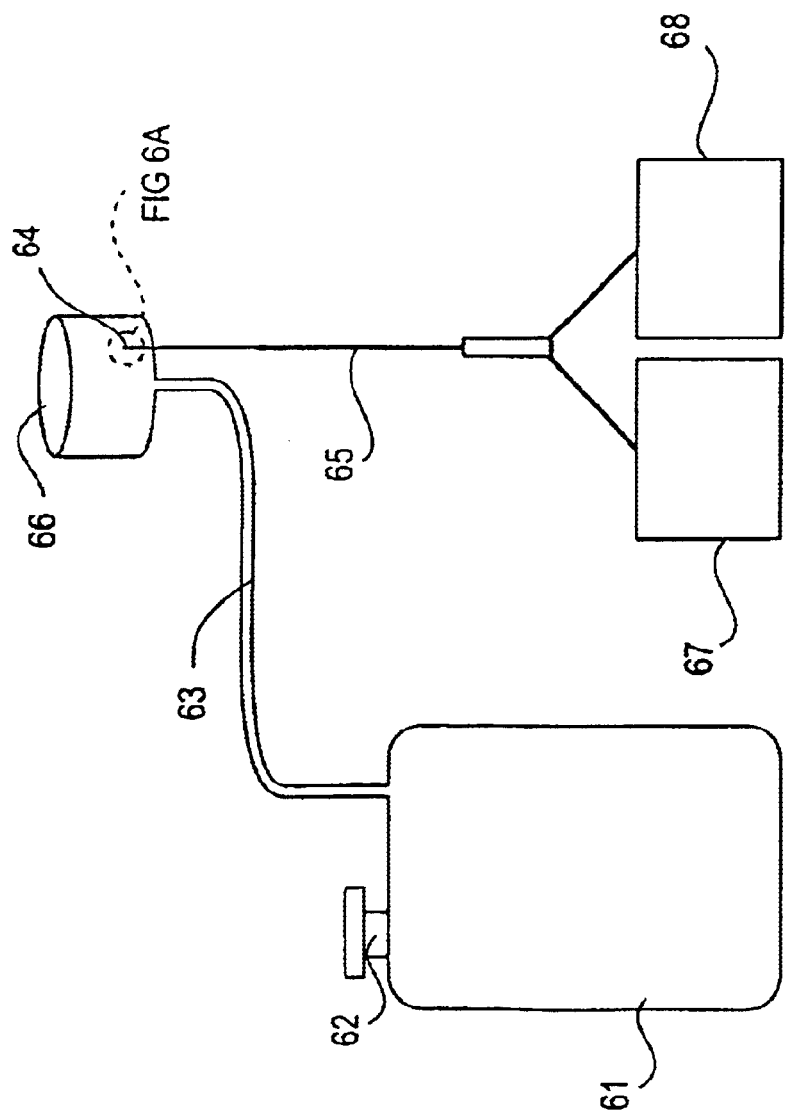
FIG. 6A
FIG. 6

5-(4-boronophthaloyl-amidophenyl)-10,15,20-(4-ethenylphenyl)3-porphyrinato copper(II).

CORTISOL SENSOR

CROSS-REFERENCE TO RELATED APPLICATIONS

The present application claims the benefit of prior filed Provisional Application No. 60/383,543 which was filed with the United States Patent and Trademark Office on May 28, 2002. The entire disclosure of the above-referenced application is incorporated herein by reference.

BACKGROUND OF THE INVENTION

1. Field of the Invention

The present invention relates generally to sensor devices comprising molecularly imprinted polymers for use in real-time detection of cortisol levels in a fluid sample, and methods for using such devices to detect cortisol levels in real time.

2. Description of the Related Art

Methods and apparatus for the efficient and accurate detection and quantification of cortisol (or hydrocortisone) levels are of particular interest for use in a wide range of applications. For example, because cortisol (a steroid produced in the human body by the adrenal gland) is known to be a regulator of many biological functions, has been identified as a biomarker for many diseases (e.g. Cushing's Syndrome), and has been correlated with levels of stress, the measurement of cortisol in the human body is an important tool for use in clinical diagnostics and in monitoring stress levels during stress-intensive activities.

Presently, applicants have discovered that for many cortisol-detecting applications, the development of portable, non-invasive sensor devices, which are relatively highly-selective and sensitive to the detection of cortisol, and are capable of monitoring cortisol levels in real-time, is of particular interest. For example, there is a military interest in measuring the relative stress levels of soldiers in combat situations. Because cortisol levels in the body tend to fluctuate both throughout the day (cortisol levels tend to be higher in the morning and lower in the evening), and in response to dietary intake and/or metabolic imbalances, it is imperative in combat situations for cortisol measurements to be measured continually and without substantial delay if useful and effective monitoring of the stress and fatigue of a soldier in the field is to be maintained.

Unfortunately, many conventional methods for detecting cortisol levels in the body are incapable of continuous real-time monitoring and/or are highly invasive. For example, a variety of conventional methods for the unambiguous detection of specific cortisol levels in the body require drawing a sample of blood and having the sample processed and analyzed in a laboratory. Much of the technology and laboratory equipment used for such analysis, including gas chromatography-mass spectroscopy (GC-MS) and high performance liquid chromatography (HPLC), are large (not portable), expensive, and/or require sophisticated, often extensive analysis procedures making them undesirable for real-time field analysis. Although these techniques have some degree of sensitivity, they lack specificity, rapid detection, real time analysis, easy operation, low cost, and portability. They also tend to be relatively invasive to the body.

Certain other conventional devices, such as saliva collection kits, are available commercially and are capable of measuring cortisol levels in collected saliva samples. However, such kits are disadvantageous in that they still require lab processing and the time associated therewith.

Recognizing these and other disadvantages and drawbacks associated with conventional sensing methods and apparatus, applicants have developed the present invention.

SUMMARY OF THE INVENTION

The present invention overcomes the aforementioned disadvantages by providing sensor devices that are capable of real-time measurement of cortisol levels in a sample, and also offer the advantages of high selectivity, high sensitivity, easy operation, low cost, and portability. As used herein the term "real-time measurement of cortisol levels" or "real-time" refers to the relatively rapid detection of cortisol levels in a fluid sample freshly produced from a body so as to indicate current or near current cortisol level data for the body. In certain embodiments of the present invention, the real-time measurement of cortisol levels comprises a time delay, from the production of a fresh sample from a human body, for example, via salivation, expectoration, urination, and the like, to the detection of the cortisol levels in the produced sample, of about 15 minutes or less. Preferably, the time delay is about 5 minutes or less, and more preferably 1 minute or less. In certain other embodiments, the "real-time measurement" can be obtained with substantially no delay.

Applicants have discovered that molecularly imprinted polymers (MIPs) capable of binding with cortisol molecules can be used to great advantage in sensor devices designed to detect varying levels of cortisol in the human body in real-time. In particular, applicants have discovered that MIPs according to the present invention can be advantageously adapted for use with a wide variety of light sources and detectors to produce cortisol sensor devices which are able to detect cortisol molecules with a relatively high degree of selectivity and sensitivity, and in less time and with fewer false positives than conventional optical sensors. In addition, applicants have discovered that the MIPs of the present invention can be incorporated in low-cost, portable devices capable of being used in the field to provide real-time measurements of cortisol levels in the human body.

According to one aspect of the present invention, provided are sensor devices for detecting cortisol molecules. In certain preferred embodiments, the sensor devices of the present invention comprise a molecularly imprinted polymer comprising a cortisol-binding chromophore operatively associated with a source of excitation energy for the chromophore; and a detector for detecting fluorescent energy emitted upon chromophore excitation.

According to certain other aspects of the present invention, provided are methods of detecting cortisol molecules in real-time by using a sensor device of the present invention.

BRIEF DESCRIPTION OF THE DRAWINGS

FIG. 1 is a schematic drawing of an optical sensor according to one embodiment of the present invention.

FIG. 4 depicts the structural representation of an optical sensor according to certain preferred embodiments of the present invention.

FIG. 5 depicts the structural representation of an optical sensor according to certain other preferred embodiments of the present invention.

FIG. 6 depicts the structural representation of a reservoir-containing optical sensor according to certain preferred embodiments of the present invention.

DETAILED DESCRIPTION

The present invention provides optical sensors that employ a molecularly imprinted polymer containing a chromophore, in conjunction with a light source and a detector, to detect cortisol molecules with a relatively high degree of selectivity and sensitivity.

Figure 2:
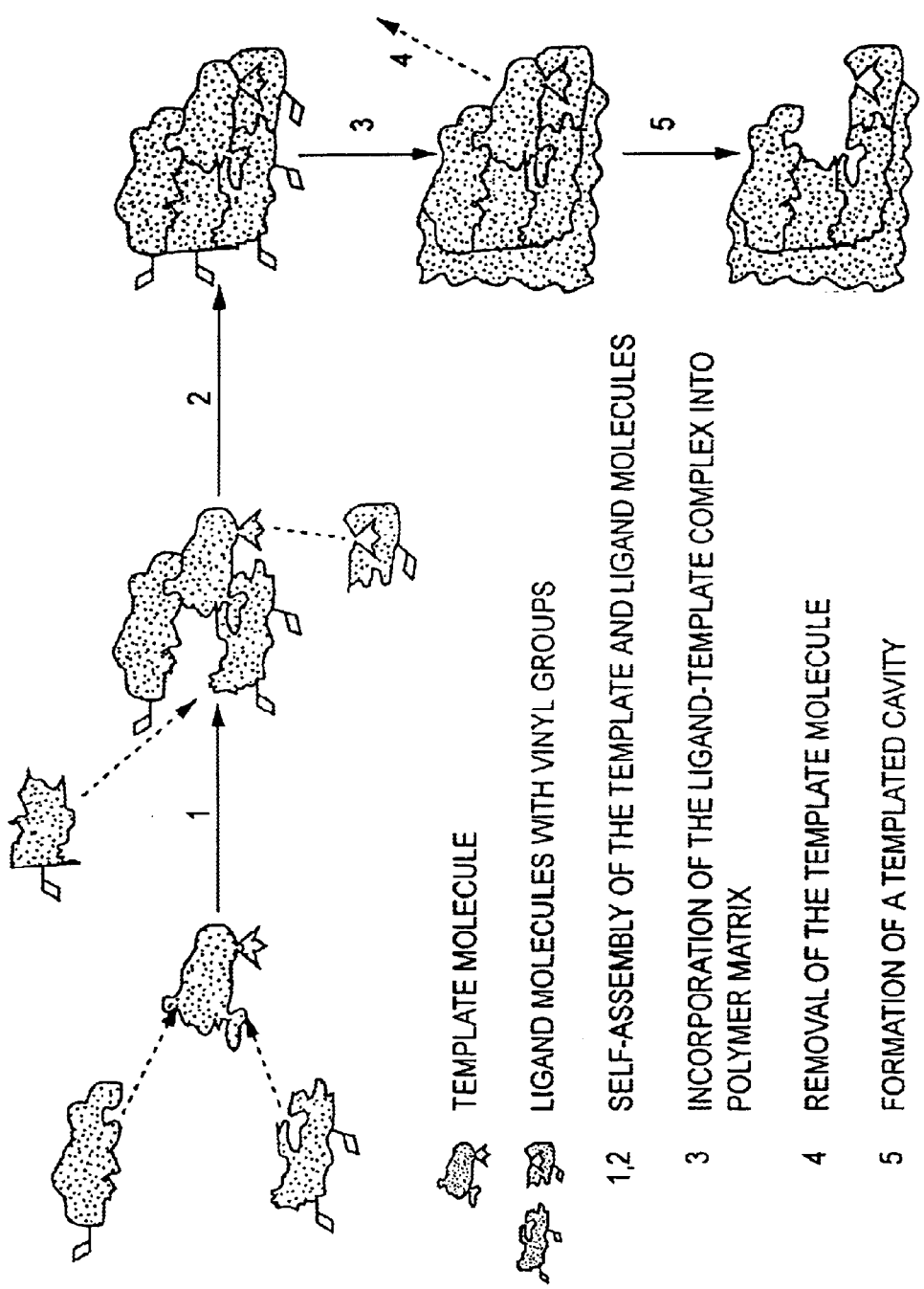
FIG. 2 is a schematic representation of molecular imprinting to obtain a molecularly imprinted polymer according to certain embodiments of the present invention.

As used herein, the term "molecularly imprinted polymer" or "MIP" refers generally to a polymeric template-like structure having one or more pre-organized recognition sites which complement the shape of at least a portion of a target or imprint molecule and which contain interactive moieties that complement the spacing of, and exhibit an affinity for, at least a portion of the binding sites on the target or imprint molecule. As will be recognized by those of skill in the art, MIPs are typically formed by binding imprint molecules to one or more functional monomers to form imprint/monomer complexes (wherein "binding" means the imprint molecule interacts, coordinates, and/or bonds with a complementary moiety of the functional monomer via covalent, ionic, hydrophobic, steric, electostatic, hydrogen-bonding, or other interactions). The monomer/imprint complexes are then polymerized into a highly cross-linked polymer matrix, and the imprint molecules are subsequently dissociated from the functional monomers and removed from the polymer matrix to leave cavities or recognition sites that are relatively shape specific to the imprint molecules and which contain complementary moieties having the ability to rebind chemically with the imprint molecule. FIG. 2 is a schematic representation of one method of molecular imprinting showing self assembly of an imprint to form a imprint complex (1,2); incorporation of the imprint complex into the polymer matrix (3); removal of the imprint molecule; and formation of the imprinted cavity (5).

The combination of the shape specificity of the cavities formed in the MIP and the affinity of the moieties associated with the MIP cavities for the target molecule results in the polymer exhibiting selective binding characteristics for the imprint substance. The terms "selective binding characteristics" and "selective binding interactions" are intended to refer to preferential and reversible binding exhibited by an imprinted polymer for its imprint molecule compared to other non-imprint molecules. Selective binding includes both affinity and specificity of the imprinted polymer for its template molecule.

According to certain embodiments, the MIPs of the present invention comprise chromophore-containing polymeric structures that exhibit selective binding characteristics towards cortisol molecules to be detected by a sensor device of the present invention. Applicants have recognized that such MIPs can be used advantageously as part of an optical sensor device to selectively capture cortisol molecules, by associating such molecules with the MIP chromophore binding sites, from a solution containing cortisol molecules for detection by the sensor. The present MIPs act not only to provide a site for selectively rebinding cortisol molecules, but also, act as a source of fluorescence, which can be analyzed to determine the amount of cortisol in a fluid sample. As cortisol molecules are associated with the chromophores in the present MIPs, the intensity of a certain fluorescence line will vary with the amount of cortisol bound to the polymer. Such characteristic fluorescence can be detected and analyzed to determine the amount of cortisol in fluid sample according to the present invention.

Figure 3:
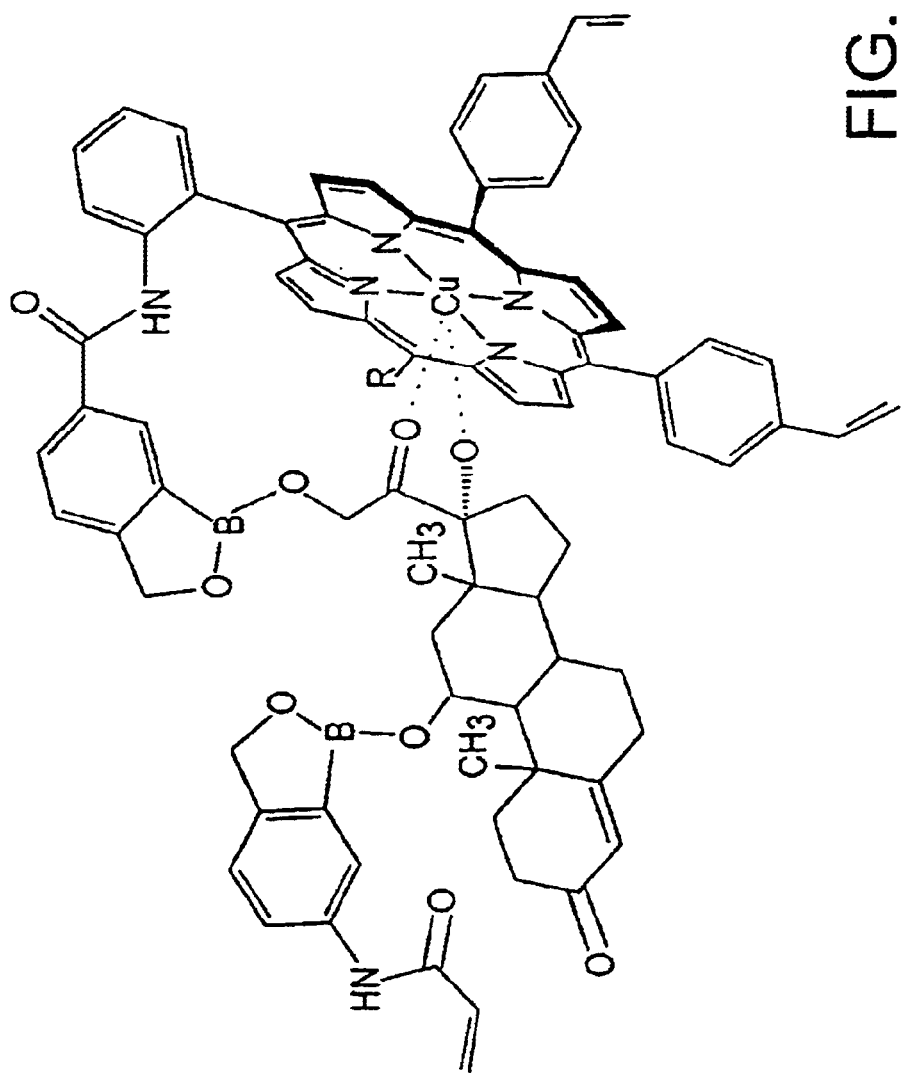
FIG. 3 depicts a structural representation of an exemplary cortisol-chromophore complex according to one embodiment of the present invention.

An MIP exhibiting selective binding characteristics towards cortisol molecules in accordance with the principles of the present invention can be prepared by adapting for use herein any of a wide range of known methods including those described in U.S. Pat. Nos. 5,110,883; 5,321,102; 5,372,719; 5,310,648; 5,208,155; 5,015,576; 4,935,365; 4,960,762; 4,532,232; 4,415,655; and 4,406,792, as well as, U.S. patent application Ser. No. 09/300,867, "Imprinted Polymers as Protecting Groups for Regioselective Modification of Polyfunctional Substrates" C. Alexander et al., *J. Amer. Chem. Soc.*, 1999, 121,6640–6651, and "Chromatographic characterization of a molecular imprinted polymer binding cortisol" Baggiani et al., *Talanta*, 2000, 51, 71–75, the entire disclosures of which are incorporated herein by reference. According to certain preferred embodiments, MIPs of the present invention are formed by: preparing a cortisol-chromophore complex, co-polymerizing the cortisol-chromophore complex with one or more cross-linking monomers, and optionally, one or more matrix monomers to form a polymer structure, and removing the cortisol molecule from the polymer structure to form an MIP. As used herein, the term "cortisol-chromophore complex" refers generally to a complex comprising a cortisol molecule chemically bonded to a chromophore, the bonded chromophore having one or more polymerizable moieties attached thereto. By way of example, FIG. 3 shows a complex (wherein R is para-vinyl phenyl) comprising a cortisol molecule reversibly and covalently bonded to a styrene-substituted porphyrin chromophore (5-(4-boronopthaloyl-amidophenyl)-10,15,20-(4-ethenylphenyl)$_3$-porphyrinato copper(II) via the boronophthalide binding group according to certain preferred embodiments of the present invention. The term "chemically bonded," as used herein, refers generally to any two moieties that are associated via covalent, ionic, hydrophobic, steric, electrostatic, or hydrogen bonding, or other bonding interactions.

Any of a wide range of chromophores capable of reversibly binding to a cortisol molecule (through attached binding groups and/or via metal substitution) and having one or more polymerizable moieties attached thereto are suitable for use in the present invention. Suitable chromophores include, for example, molecules comprising porphyrins, phthalocyanines, aromatic ruthenium complexes, other organometallic complexes, combinations of two or more thereof, and the like, having one or more polymerizable moieties attached thereto, and optionally, one or more binding groups for binding the chromophore to a cortisol molecule. The polymerizable moieties may be any moieties/substituents capable of binding to the chromophore and capable of being polymerized with one or more other polymerizable monomers while bonded to a chromophore of the present invention. Examples of suitable polymerizable moieties include substituted or unsubstituted unsaturated groups such as styryl groups, as well as, unsaturated substituents disclosed in U.S. Pat. Nos. 5,371,199, 5,493,017, 5,599,924, which patents are incorporated herein in by reference, and the like. The binding groups may comprise any moieties capable of binding a cortisol molecule to the chromophore while maintaining the fluorescent properties of the chromophore. Examples of suitable binding moieties include boronophthalides, and the like. Certain preferred chromophores of the present invention include substituted porphyrins such as, for example, 5-(4-boronopthaloyl-amidophenyl)-10,15,20-(4-ethenylphenyl)$_3$-porphyrinato copper(II), as well as, substituted cortisol-binding porphyrins disclosed in U.S. Pat. Nos. 5,371,199, 5,493,017, 5,599,924, which patents are incorporated herein in by reference, and the like. In certain particularly preferred embodiments, the chromophore is 5-(4-boronopthaloyl-amidophenyl)-10,15,20-(4-ethenylphenyl)$_3$-porphyrinato copper(II).

Figure 8:
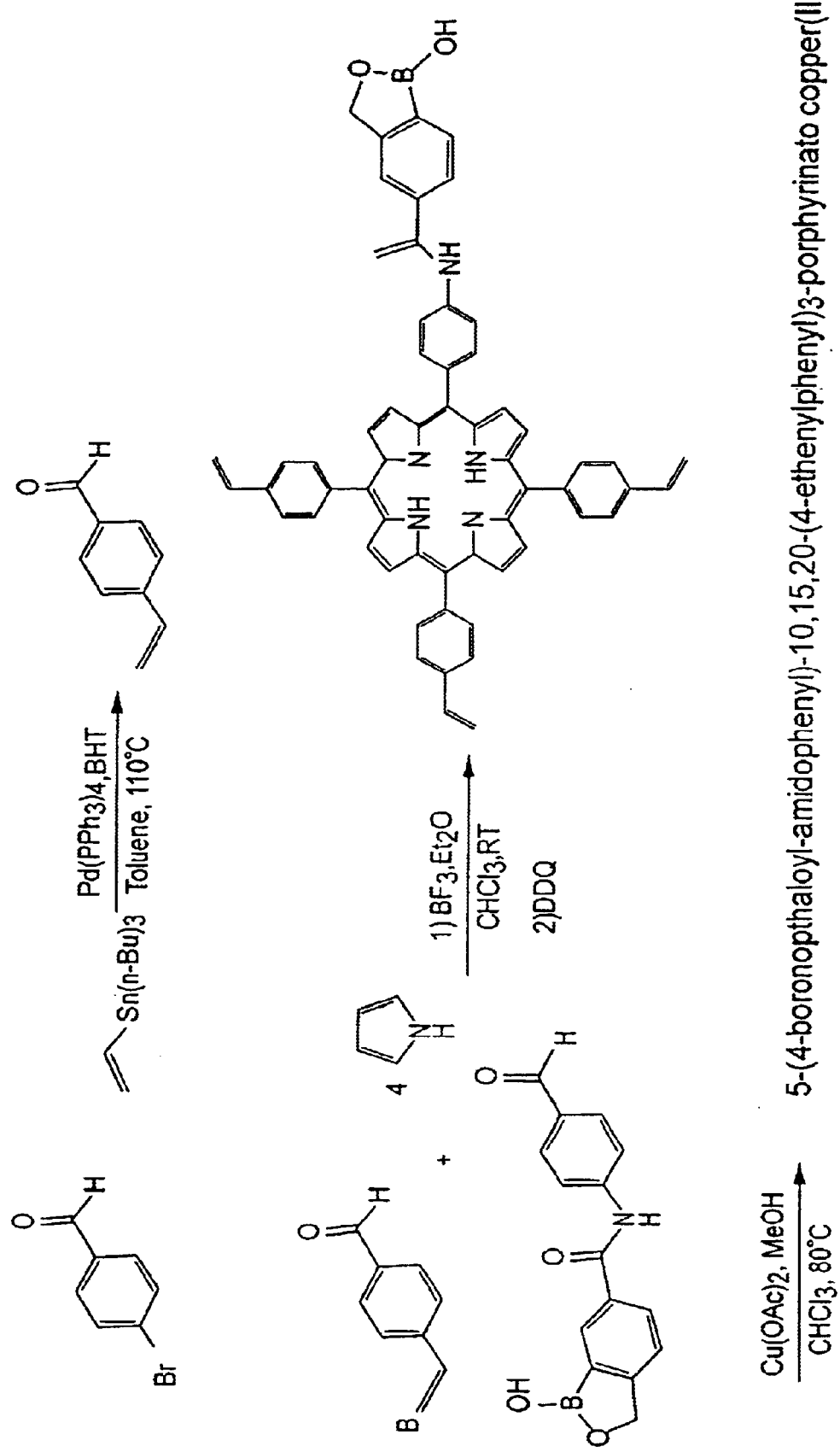
FIG. 8 depicts the reaction scheme for producing a chromophore according to certain embodiments of the present invention.

Many suitable chromophores can be readily prepared using techniques known to those of skill in the art. For example, methods for synthesizing porphyrins and substituted derivatives thereof are disclosed in Wagner, R. W., Lawrence, D. S. and Lindsey, J. S., "An Improved Synthesis of Tetramesitylporphyrin" *Tet. Lett.*, 1987, 28, pp.3069–70.; Lindsey, J. S., Schreiman, I. C., Hsu, H. C., Kearney, P. C., Marguerettaz, A. M., *J Org. Chem.* 1987, 52, 827–836; Lawrence, D. S. "Studies of Picket Fence Porphyrins and Substituted Metallo-Phthalocyanines," Dissertation, University of Rochester, 1994 and U.S. Pat. Nos. 5,371,199, 5,493,017, 5,599,924, all of which are incorporated herein by reference. By way of further example, the synthesis of a preferred porphyrin chromophore, 5-(4-boronopthaloyl-amidophenyl)-10,15,20-(4-ethenylphenyl)$_3$-porphyrinato copper(II), according to certain embodiments of the present invention is depicted schematically in FIG. 8. As shown in FIG. 8, stoichiometric amounts of 4-vinylbenzaldehyde (synthesized as in McKean, D. R.; Parinello, G.; Renaldo, A. F.; Stille, J. K., "Synthesis of functionalized styrenes via palladium-catalyzed coupling of aryl bromides with vinyl tin reagents" *J. Org. Chem.*, 1987, 52, 422–424, incorporated herein by reference), 4-boronophthalidylamido-benzaldehyde and pyrrole in chloroform are reacted with a catalytic amount of boron trifluoride etherate at room temperature to form the intermediate porphyrinogen. This intermediate is then oxidized with 2,3-dichloro-5,6-dicyano-1,4-benzoquinone (DDQ) to form the derivatized porphyrin which is substituted with polymerizable styrene groups. It will be apparent to those skilled in the art that alternate pathways to synthesizing the product depicted in FIG. 8 are possible, and are within the scope of this invention.

In certain preferred embodiments, cortisol-chromophore complexes of the present invention are made by mixing and/or reacting stoichiometric amounts of cortisol molecules with one or more chromophores having one or more polymerizable moieties attached thereto. As will be recognized by those of skill in the art, the particular amounts of cortisol and chromophore to be used and the conditions under which the complex components are mixed and/or reacted will depend, at least in part, on a number of factors including the particular chromophore used to form the complex and the number sites thereon available for binding to cortisol. According to certain embodiments, it is preferred to form the complex using amounts of cortisol and chromophore effective to bind each of the three reactive hydroxyl sites on the cortisol molecules to one or more chromophores. For example, in embodiments wherein the chromophore comprises a boronphthalide binding group, it is preferred to react cortisol with the chromophore under dehydration conditions, such as those disclosed in "Imprinted Polymers as Protecting Groups for Regioselective Modification of Polyfunctional Substrates" C. Alexander et al., *J. Amer. Chem. Soc.*, 1999, 121,6640–6651 to form a complex wherein each cortisol molecule is bound to three boronphthalide binding groups (as shown previously in FIG. 3).

In light of the disclosure herein, those of skill in the art will be readily able to produce a variety of cortisol-chromophore complexes suitable for use in a wide range of applications according to the present invention without undue experimentation.

According to certain embodiments of the present invention, the polymerization step comprises co-polymerizing a cortisol-chromophore complex with one or more cross-linking monomers, and optionally, one or more additional matrix monomers to form a polymer structure. Any of a wide range of crosslinking monomers can be used according to the present invention. Suitable crosslinking monomers/agents that lend rigidity to the MIP are known to those skilled in the art, and include di-, tri- and tetrafunctional acrylates or methacrylates, divinylbenzene (DVB), alkylene glycol and polyalkylene glycol diacrylates and methacrylates, including ethylene glycol dimethacrylate (EGDMA) and ethylene glycol diacrylate, vinyl or allyl acrylates or methacrylates, divinylbenzene, diallyldiglycol dicarbonate, diallyl maleate, diallyl fumarate, diallyl itaconate, vinyl esters such as divinyl oxalate, divinyl malohate, diallyl succinate, triallyl isocyanurate, the dimethacrylates or diacrylates of bis-phenol A or ethoxylated bis-phenol A, methylene or polymethylene bisacrylamide or bismethacrylamide, including hexamethylene bisacrylamide or hexamethylene bismethacrylamide, di(alkene) tertiary amines, trimethylol propane triacrylate, pentaerythritol tetraacrylate, divinyl ether, divinyl sulfone, diallyl phthalate, triallyl melamine, 2-isocyanatoethyl methacrylate, 2-isocyanatoethylacrylate, 3-isocyanatopropylacrylate, 1-methy:L-2-isocyanatoethyl methacrylate, 1,1-dimethyl-2 isocyanaotoethyl acrylate, tetraethylene glycol diacrylate, tetraethylene glycol dimethacrylate, triethylene glycol diacrylate, triethylene glycol dimethacrylate, hexanediol dimethacrylate, hexanediol diacrylate, and the like.

Any suitable monomer that provides an accurate imprint of the imprint molecule upon polymerization may be optionally used in addition to the crosslinking monomers and cortisol-chromophore complexes to synthesize a MIP in accordance with the principles of the present invention. Examples of suitable monomers include any of the complexing ligand monomers described above for forming a cortisol-chromophore complex. Further suitable non-limiting examples of monomers that can be used for preparing an MIP of the present invention include: methylmethacrylate, other alkyl methacrylates, alkylacrylates, allyl or aryl acrylates and methacrylates, cyanoacrylate, styrene, alpha-methyl styrene, vinyl esters, including vinyl acetate, vinyl chloride, methyl vinyl ketone, vinylidene chloride, acrylamide, methacrylamide, acrylonitrile, methacrylonitrile, 2-acetamido acrylic acid; 2-(acetoxyacetoxy)ethyl methacrylate 1-acetoxy-1,3-butadiene; 2-acetoxy-3-butenenitrile; 4-acetoxystyrene; acrolein; acrolein diethyl acetal; acrolein dimethyl acetal; acrylamide; 2-acrylamidoglycolic acid; 2-acrylamido-2-methyl propane sulfonic acid; acrylic acid; acrylic anhydride; acrylonitrile; acryloyl chloride; (R)-alpha-acryloxy-beta, beta'-dimethyl-g-butyrolactone; N-acryloxy succinimide N-acryloxytris(hydroxymethyl) aminomethane; N-acryloyl chloride; N-acryloyl pyrrolidinone; N-acryloyltris(hydroxymethyl)amino methane; 2-amino ethyl methacrylate; N-(3 aminopropyl)methacrylamide; (o, m, or p)-amino-styrene; t-amyl methacrylate; 2-(1aziridinyl) ethyl methacrylate; 2,2'-azobis-(2-amidinopropane); 2,2'-azobisisobutyronitril 4,4'-azobis-(4-cyanovaleric acid); 1,1'-azobis-(cyclohexanecarbonitrile); 2,2'-azobis-(2,4 dimethylvaleronitrile); 4-benzyloxy-3-methoxystyrene; 2-bromoacrylic acid; 4-bromo-1-butene; 3-bromo-3,3- difluoropropane; 6-bromo-1-hexene; 3-bromo-2-methacrylonitrile; 2-(bromomethyl)acrylic acid; 8-bromo-1-octene; 5-bromo-1-pentene; cis-1-bromo-1-propene; beta-bromostyrene; p-bromostyrene; bromotrifluoro ethylene; (t)-3-buten-2-ol; 1,3-butadiene; 1,3-butadiene-1,4-dicarboxylic acid; 3-butenal diethyl acetal; 1-butene; 3 buten-2-ol; 3-butenyl chloroformate; 2-butylacrolein; N-t-butylacrylamide; butyl acrylate; butyl methacrylate; (o,m,p)-bromostyrene; t-butyl acrylate; (R)-carvone; (S)-carvone; (−)-carvyl acetate; cis-3-chloroacrylic acid; 2-chloroacrylonitrile; 2-chloroethyl vinyl ether; 2-chloromethyl-3-trimethylsilyl-1-propene; 3-chloro-1-butene; 3-chloro-2-chloromethyl-1-propene; 3-chloro-2-methyl propene; 2,2-bis(4-chlorophenyl)-1,1-dichloroethylene; 3-chloro-1-phenyl-1-propene; m-chlorostyrene; o-chlorostyrene; p-chlorostyrene; 1-cyanovinyl acetate; 1-cyclopropyl-1-(trimethylsiloxy) ethylene; 2,3-dichloro-1-propene; 2,6-dichlorostyrene; 1,3-dichloropropene; 2,4-diethyl-2,6-heptadienal; 1,9-decadiene; 1-decene; 1,2-dibromoethylene; 1,1-dichloro-2,2-difluoroethylene; 1,1-dichloropropene; 2,6 difluorostyrene; dihydrocarveol; (±)-dihydrocarvone; (−)-dihydrocarvyl acetate; 3,3-dimethylacrylaldehyde; N,N'-dimethylacrylamide; 3,3-dimethylacrylic acid; 3,3-dimethylacryloyl chloride; 2,3-dimethyl-1-butene; 3,3-dimethyl-1-butene; 2-dimethylaminoethyl methacrylate; 2,4-dimethyl-2,6-heptadien-1-ol; 2,4-dimethyl-2,6-heptadienal; 2,5-dimethyl-1,5-hexadiene; 2,4-dimethyl-1,3-pentadiene; 2,2-dimethyl-4-pentenal; 2,4dimethylstyrene; 2,5-dimethylstryene; 3,4-dimethylstryene; divinyl benzene; 1,3-divinyltetramethyl disiloxane; 8,13-divinyl-3,7,12,17-tetramethyl-21H,23H-porphine; 8,13-divinyl-3,7,12,17-tetramethyl-21H,23H-propionic acid; 8,13-divinyl-3,7,12,17-tetramethyl-21H,23H-propionic acid disodium salt; 3,9-divinyl-2,4,8,10-tetraoraspiro[5,5]undecane; divinyl tin dichloride; 1-dodecene; 3,4-epoxy-1-butene; 2-ethyl acrolein; ethyl acrylate; 2-ethyl-1-butene; (±)-2-ethylhexyl acrylate; (±)-2-ethylhexyl methacrylate; 2-ethyl-2-(hydroxymethyl)-1,3-propanediol triacrylate; 2-ethyl (hydroxymethyl)-1,3-propanediol trimethacrylate; ethyl methacrylate; ethyl vinyl ether; ethyl vinyl ketone; ethyl vinyl sulfone; (1-ethylvinyl)tributyl tin; m-fluorostyrene; o-fluorostyrene; p-fluorostyrene; glycol methacrylate (hydroxyethyl methacrylate); 1,6-heptadiene; 1,6-heptadienoic acid; 1,6-heptadien-4-ol; 1-heptene; 1-hexen-3-ol; 1-hexene; hexafluoropropene; 1,6-hexanediol diacrylate; 1-hexadecene; 1,5-hexadien-3,4 diol; 1,4-hexadiene; 1,5-hexadien-3-ol; 1,3,5-hexatriene; 5-hexen-1,2-diol; 5-hexen-1-ol; hydroxypropyl acrylate; 3-hydroxy-3,7,11-trimethyl-1,6,10-dodecatriene; isoamyl methacrylate; isobutyl methacrylate; isoprene; 2-isopropenylaniline; isopropenyl-chloroformate; 4,4'-isopropylidene dimethacrylate; 3-isopropyl-a-a-dimethylbenzene isocyanate; isopulegol; itaconic acid; itaconalyl chloride; lead (11) acrylate; (t)-:linalool; linalyl acetate; p-mentha-1,8-diene; p-mentha-6,8-dien-2-ol; methyleneamino acetonitrile; methacrolein; [3-(methacryloylamino)-propyl]trimethylammonium chloride; methacrylamide; methacrylic acid; methacrylic anhydride; methacrylonitrile; methacryloyl chloride; 2-(methacryloyloxy)ethyl acetoacetate; (3-methacryloxypropyl)trimethoxy silane; 2-(methacryloxy) ethyl trimethyl ammonium methylsulfate; 2-methoxy propene (isopropenyl methyl ether); methyl-2-(bromomethyl) acrylate; 5-methyl-5-hexen-2-one; methyl methacrylate; N,N'-methylene bisacrylamide; 2-methylene glutaronitrite; 2-methylene-1,3-propanediol; 3-methyl-1,2-butadiene; 2-methyl-1-butene; 3-methyl-1-butene; 3-methyl-1-buten-1-ol; 2-methyl-1-buten-3-yne; 2-methyl-1,5-heptadiene; 2methyl-1-heptene; 2-methyl-1-hexene; 3-methyl-1,3-pentadiene; 2-methyl-1,4-pentadiene; (±)-3-methyl-1-pentene; (±)-4-methyl-1-pentene; (±)-3-methyl-1-penten-3-ol; 2-methyl-1-pentene; alpha-methyl styrene; t-a-methylstyrene; t-beta-methylstyrene; 3-methylstyrene; methyl vinyl ether; methyl vinyl ketone; methyl-2-vinyloxirane; 4 methylstyrene; methyl vinyl sulfonee; 4-methyl5-vinylthiazole; myrcene; t-beta-nitrostyrene; 3-nitrostyrene; 1-nonadecene; 1,8-nonadiene; 1-octadecene; 1,7-octadiene; 7 octene-1,2-diol; 1-octene; 1-octen-3-ol; 1-pentadecene; 1-pentene; 1-penten-3-ol; t-2,4 pentenoic acid; 1,3-pentadiene; 1,4-pentadiene; 1,4-pentadien-3-ol; 4-penten-1-ol; 4 penten-2-ol; 4-phenyl-1-butene; phenyl vinyl sulfide; phenyl vinyl sulfonate; 2-propene-1 sulfonic acid sodium salt; phenyl vinyl sulfoxide; 1-phenyl-1-(trimethylsiloxy)ethylene; propene; safrole; styrene (vinyl benzene); 4-styrene sulfonic acid sodium salt; styrene sulfonyl chloride; 3-sulfopropyl acrylate potassium salt; 3-sulfopropyl methacrylate sodium salt; tetrachloroethylene; tetracyano ethylene; tetramethyldivinyl siloxane; trans 3chloroacrylic acid; 2-trifluoromethyl propene; 2-(trifluoromethyl)propenoic acid; 2,4,4'trimethyl-1-pentene; 3,5-bis(trifluoromethyl)styrene; 2,3-bis (trimethylsiloxy)-1,3-butadiene; 1-undecene; vinyl acetate; vinyl acetic acid; 4-vinyl anisole; 9-vinyl anthracene; vinyl behenate; vinyl benzoate; vinyl benzyl acetate; vinyl benzyl alcohol; 3-vinyl benzyl chloride; 3-(vinyl benzyl)-2-chloroethyl sulfone; 4-(vinyl benzyl)-2-chloroethyl sulfone; N-(p-vinyl benzyl)-N,N'-dimethyl amine; 4-vinyl biphenyl (4-phenyl styrene); vinyl bromide; 2-vinyl butane; vinyl butyl ether; 9-vinyl carbazole; vinyl carbinol; vinyl cetyl ether; vinyl chloroacetate; vinyl chloroformate; vinyl crotanoate; vinyl cyclohexane; 4vinyl-1-cyclohexane; 4-vinylcyclohexene dioxide; vinyl cyclopentene; vinyl dimethylchlorosilane; vinyl dimethylethoxysilane; vinyl diphenylphosphine; vinyl 2-ethyl hexanoate; vinyl 2-ethylhexyl ether; vinyl ether ketone; vinyl ethylene; vinyl ethylene iron tricarbonyl; vinyl ferrocene; vinyl formate; vinyl hexadecyl ether; vinylidene fluoride; Ivinyl imidizole; vinyl iodide; vinyl laurate; vinyl magnesium bromide; vinyl mesitylene; vinyl 2-methoxy ethyl ether; vinyl methyl dichlorosilane; vinyl methyl ether; vinyl methyl ketone; 2-vinyl naphthalene; 5-vinyl-2-norbomene; vinyl pelargonate; vinyl phenyl acetate; vinyl phosphonic acid, bis(2-chloroethyl)ester; vinyl propionate; 4-vinyl pyridine; 2-vinyl pyridine; 1-vinyl-2-pyrrolidinone; 2-vinyl quinoline; 1-vinyl silatrane; vinyl sulfone; vinyl sulfone (divinylsulfone); vinyl sulfonic acid sodium salt; o-vinyl toluene; pvinyl toluene; vinyl triacetoxysilane; vinyl tributyl tin; vinyl trichloride; vinyl trichlorosilane; vinyl trichlorosilane (trichlorovinylsilane); vinyl triethoxysilane; vinyl triethylsilane; vinyl trifluoroacetate; vinyl trimethoxy silane; vinyl trimethyl nonylether; vinyl trimethyl silane; vinyl triphenylphosphonium bromide (triphenyl vinyl phosphonium bromide); vinyl tris-(2-methoxyethoxy)silane; vinyl 2-valerate and the like. Acrylate-terminated or otherwise unsaturated urethanes, carbonates, and epoxides can also be used in the MIP. An example of an unsaturated carbonate is allyl diglycol carbonate (CR-39). Unsaturated epoxides include, but are not limited to, glycidyl acrylate, glycidyl methacrylate, allyl glycidyl ether, and 1,2-epoxy-3-allyl propane.

Preferred examples of matrix monomers include styrene, or styrene derivatives, divinylbenzene, methylacrylate, and the like. In certain embodiments, styrene, styrene derivatives, methacrylates, and the like are particularly preferred.

Any ratio of simple monomers to crosslinking monomers that provides a polymeric structure of appropriate integrity can be used to produce an MIP according to the present invention. In light of the disclosure herein, those skilled in the art will be readily able to select suitable ratios of monomers to provide the desired structural integrity and produce MIPs according to the present invention, without undue experimentation.

Any suitable conditions effective to polymerize the monomers of the present invention to produce an MIP without dissociating the cortisol-chromophore complex may be used. The monomers of the present invention may be polymerized via cationic polymerization, anionic polymerization, free radical polymerization, and the like. In preferred embodiments, thermal and/or free radical polymerization is used.

When polymerization is complete, the crosslinked polymer may be washed, cryogenically ground to a uniformly fine powder, and/or extensively eluted with solvents to remove any un-reacted cortisol-chromophore complex. The steps of grinding and/or freezing in liquid nitrogen may be used to maximize surface area and allow for access by the various reagents and samples. Freezing allows the polymer to become brittle enough to be ground and prevents distortions of the polymer by the heat of friction. Polymers used in the construction of optical sensors may be prepared in situ on the distal end of an optical fiber whose surface is prepared by binding a polymerizable agent on the surface.

After polymerization, the cortisol molecule may be removed in a manner that does not adversely affect the imprinted cavity. In embodiments wherein the cortisol molecule is covalently bound to the functional monomer, any appropriate method can be used to cleave the covalent bond, although the covalent bond formed should preferably be cleaved under conditions suitable to release the cortisol molecule after the MIP is formed, without adversely affecting the selective binding characteristics of the MIP. To accomplish this, acetone or other suitable organic solvent may be used to swell the resultant polymers, allowing greater access to the coordinated chromophores because imprinted resins have a relatively low amount of functionalization and are primarily nonionic matrices. The covalent bond that is cleaved to release the cortisol molecule can optionally provide an additional polar or ionic site for design and imprinting of the cortisol molecule. In certain preferred embodiments, the bound coritsol molecule is simply leached or washed out after polymerization. Any fluid capable of removing a cortisol molecule bound to a chromophore in an MIP of the present invention can be used to leach or wash the cortisol molecule according to the present invention. Suitable fluids include, for example, water, other aqueous solutions, such as dilute acids or dilute bases of sufficient pH strength as to dissociate the cortisol-chromophore complex. In certain preferred embodiments, the cortisol molecules is washed out using an aqueous solutions, and in particular, water.

According to certain other embodiments, an MIP of the present invention may be produced without the preparation of a cortisol-chromophore complex prior to polymerization. In such embodiments, one or more cortisol molecules are mixed with at least one chromophore, one or more crosslinking monomers, and optionally, one or more additional matrix monomers to form a reaction mixture and such mixture is polymerized under conditions effective to form a polymeric structure (generally as described above).

In certain preferred embodiments, the MIP of the present invention is used in conjunction with a source of excitation energy and a detector to form an optical sensor device for detecting a target analyte. Suitable sources of excitation energy include any of a wide variety of light sources known to those of skill in the art. As used herein, the term "light" refers to optical radiation, whether ultraviolet, visible or infrared. Suitable non-limiting examples of light sources include an argon laser, blue laser, tunable laser, light emitting diode (LED), combinations of two or more thereof, and the like.

Any of a wide range of suitable detectors can be used according to the present invention. Non-limiting examples of suitable detectors include a spectrophotometer, spectrometer (gas or mass), photomultiplier tube, CCD camera equipped with a monochromator, filters, the naked eye, combinations of two or more thereof, and the like.

Preferably, a sensor device of the present invention is produced by operatively associating at least one source of excitation energy, preferably a light source, and at least one detector with an MIP. For the purposes of the present invention, two objects are considered to be "operatively associated" when connected or arranged in a manner such that excitation or fluorescent energy produced by one of the objects is capable of being absorbed or detected as fluorescent energy by the other object. For example, a light source, detector and MIP of the present invention, may be operatively associated in any manner such that excitation energy from the light source is transmitted to the MIP and absorbed by a chromophore therein, and the fluorescent energy produced by the excited chromophore is transmitted to, and detected by, the detector. In addition, the components of the present sensor devices may be connected or arranged with or in any suitable medium through which excitation or fluorescent energy can be transmitted. Examples of suitable media include air, vacuum, optical devices, such as films or fibers, and combinations of two or more thereof.

According to certain preferred embodiments, the light source, MIP and detector are associated through optical fibers to provide a fiber optic sensor device. In certain embodiments, the fiber optic sensor device for detecting the presence of one or more cortisol molecules in a sample according to the present invention comprises: at least one optical fiber having a proximal end and a distal end for transmitting light energy, the proximal end being disposed within a probe housing, a molecularly imprinted polymer containing a chromophore disposed on, or bonded to, the distal end of the optical fiber means, wherein the chromophore is capable of chemically binding with a cortisol molecule, a light source for generating excitation energy, the light source being operatively associated with the optical fiber such that said excitation energy passes through said optical fiber means to the MIP, and the detector operatively associated with the optical fiber, for detecting fluorescent energy generated by the chromophore.

In certain embodiments, the distal end (working end) of the sensor may be enclosed within a semi-permeable membrane to separate the cortisol-containing media being analyzed from the probe. One function of the membrane is to separate, as far as possible, the analyte (i.e., those components in a sample that can bind to the probe) from interferants (i.e., compounds which may be present but are undesirable because they either interfere with the progress of the desired determination reactions or take part in reactions of their own which compete with those of the component sought and distort or overwhelm the signals that are to be measured).

In use, a cortisol molecule, if present, binds to the chromophore in the molecularly imprinted polymer causing it to fluoresce differently, generally with a different intensity than the unbound chromophore, under appropriate excitation. Light from the source of excitation travels along the optical fiber to its distal end where it undergoes a change caused by interaction with the chromophore. The modified light returns along the same or another fiber to the detection means which interprets the returned light signal. Detection is based on the change that occurs in the chromophore's fluorescence spectrum when a cortisol molecule binds to the chromophore.

FIG. 1 illustrates an exemplary fiber optic portable sensor device according to certain preferred embodiments of the present invention. The sensor device 10 in FIG. 1 comprises an optical fiber 11 having a proximal end disposed within a sensor housing 12 and a distal end having a molecularly imprinted polymer 13 disposed on (bonded to) the distal end of optical fiber 11. Light is emitted from light source 14 through a filter 15 to the proximal end of fiber 11 wherein the light energy is transmitted to the chromophores in the MIP 13. Any fluorescence energy generated by the chromophores travels back through fiber 11 to detector 16 which comprises a readout 17. While the exemplary device shown in FIG. 1 comprises a single housing for the detector and light source only, any suitable combination of one or more of the light source, detector, and/or MIP can be housed within one or more device housings according to the present invention.

According to certain preferred embodiments, the sensor devices of the present invention further comprise a fluid receptacle. Any suitable receptacle capable of receiving a fluid sample may be used in the devices of the present invention. Examples of suitable receptacles include mouthpieces, such as those disclosed in U.S. Pat. Nos. 6,070,767, 5,085,349, and 5,060,833, the complete disclosures of which are incorporated herein by reference, as well as, other mouthpieces, cups, bulbs, tubes, bowls, bladders, combinations of two more thereof, and the like. In certain preferred embodiments, the receptacle or the present device comprises a mouthpiece. It is contemplated that a receptacle suitable for use in the present invention may comprise any suitable material including, for example, a polymer, including an MIP of the present invention, rubber, plastic, metal, combinations of two or more thereof, and the like.

According to certain preferred embodiments, the receptacle of the present invention is in fluid communication with the MIP. As used herein a fluid receptacle "in fluid communication with the MIP" refers generally to a receptacle structure capable of receiving a fluid sample to be tested and in which the fluid sample is contacted with an MIP of the sensor device or through which the fluid sample is capable of flowing to an MIP for contact therewith. Fluid communication between a receptacle and an MIP of the present invention may be maintained through any suitable media or structure including air, tubing, a tubing assembly, combinations of two or more thereof, and the like.

For example, FIGS. 4 and 5 show two sensor devices (20 and 30, respectively) according to two different preferred embodiments of the present invention, each comprising a fluid receptacle in fluid communication with an MIP. In FIG. 4, sensor device 20 comprises a receptacle 21 having an opening 22 and an optical fiber 23 having a proximal end disposed within a sensor housing 24 and a distal end disposed within receptacle 21, said distal end having an MIP 25 disposed on (bonded to) the distal end of optical fiber 23. MIP 25 is operatively associated with light source 26 and detector 27 through optical fibers 23, 28, and 29. In operation, a fluid sample, for example saliva or urine, is introduced into receptacle 21 through opening 22 and held in contact with MIP 25 within receptacle 21 such that cortisol molecules within the fluid sample can bind to the MIP and be detected by detector 27 as described herein above. In FIG. 5, device 30 comprises a receptacle 31 having an opening 32 in fluid communication through tube 35 with an MIP 36 disposed on (bonded to) the distal end of optical fiber 33. In operation, a fluid sample, for example saliva or urine, is introduced into receptacle 31 through opening 32 and flows through the receptacle and through tube 35 to MIP 36 such that cortisol molecules within the fluid sample can bind to the MIP and be detected according to the present invention using light source 37 and detector 38.

According to certain other embodiments, the receptacle of the present invention comprises a cortisol-binding MIP. In such embodiments, it is contemplated that at least a portion the receptacle may be formed from an MIP of the present invention and/or may be coated with the MIP. The MIP-containing portion of the receptacle is then operatively associated with a source of excitation and a detector according to the present invention to provide a cortisol sensor device.

According to certain preferred embodiments, the sensor devices of the present invention further comprise a fluid reservoir in fluid communication with an MIP. A fluid reservoir for use herein can be any device capable of holding a fluid and from which the fluid is capable of flowing to an MIP of the present invention. Fluid communication between a reservoir and an MIP of the present invention may be maintained through any suitable media or structure including air, tubing, a tubing assembly, combinations of two or more thereof, and the like.

Any structure in which a fluid can be stored in fluid communication with an MIP of the present invention is suitable for use as reservoir herein. As will be recognized by those of skill in the art, the reservoir may vary in shape and size depending on volume of fluid to be stored therein. Preferably, the reservoir is a flexible device. Examples of devices adaptable for use as a reservoir include bladders, bulbs, cups, tanks, tubes combinations of two or more thereof, and the like. A reservoir suitable for use in the present invention may comprise any suitable material including, for example, rubber, plastic, metal, combinations of two or more thereof, and the like.

In certain preferred embodiments, the reservoir for use herein comprises an input port through which the reservoir can be filled or emptied, for example, for the purpose of cleaning the reservoir. A preferred input port comprises a filler spout with a cap sealable thereto.

FIG. 6 shows a preferred sensor device 60 of the present invention comprising a reservoir 61 having an input port 62, reservoir 61 being in fluid communication via tube 63 with a receptacle 66 and an MIP 64 disposed on the distal end of optical fiber 65 through which MIP 64 is operatively associated with light source 67 and detector 68. While not intending to be limiting, applicants have discovered that a reservoir in fluid communication with an MIP of the present invention can be used advantageously to store a fluid which can be passed over the MIP to remove cortisol molecules bound thereto and regenerate or prepare the MIP for a fresh measurement. For example, in use, a preferred device, such as is shown in FIG. 6, receives a fluid sample comprising one or more cortisol molecules through receptacle 66. The sample is contacted with MIP 64 to bind one or more cortisol molecules thereto and detect them. After such measurement is made, fluid can be flushed from the reservoir 61 through tubing 63 over the MIP and, optionally, out of the device, for example through receptacle 66, to remove the cortisol molecules and residual fluid sample from the MIP and prepare the device to receive and accurately measure cortisol molecules in a second sample, while avoiding contamination from the first sample.

A sensor device comprising a reservoir may be configured according to the present invention such that fluid from the reservoir is pushed or drawn from the reservoir to the MIP and/or to a receptacle via any of a wide range of methods. For example, fluid may be forced from the reservoir, through an output port, via the application of pressure at the reservoir, i.e. via compression of the reservoir, or the like. Alternatively, fluid may be drawn from the reservoir using suction (vacuum), gravity, or the like.

Figure 7:
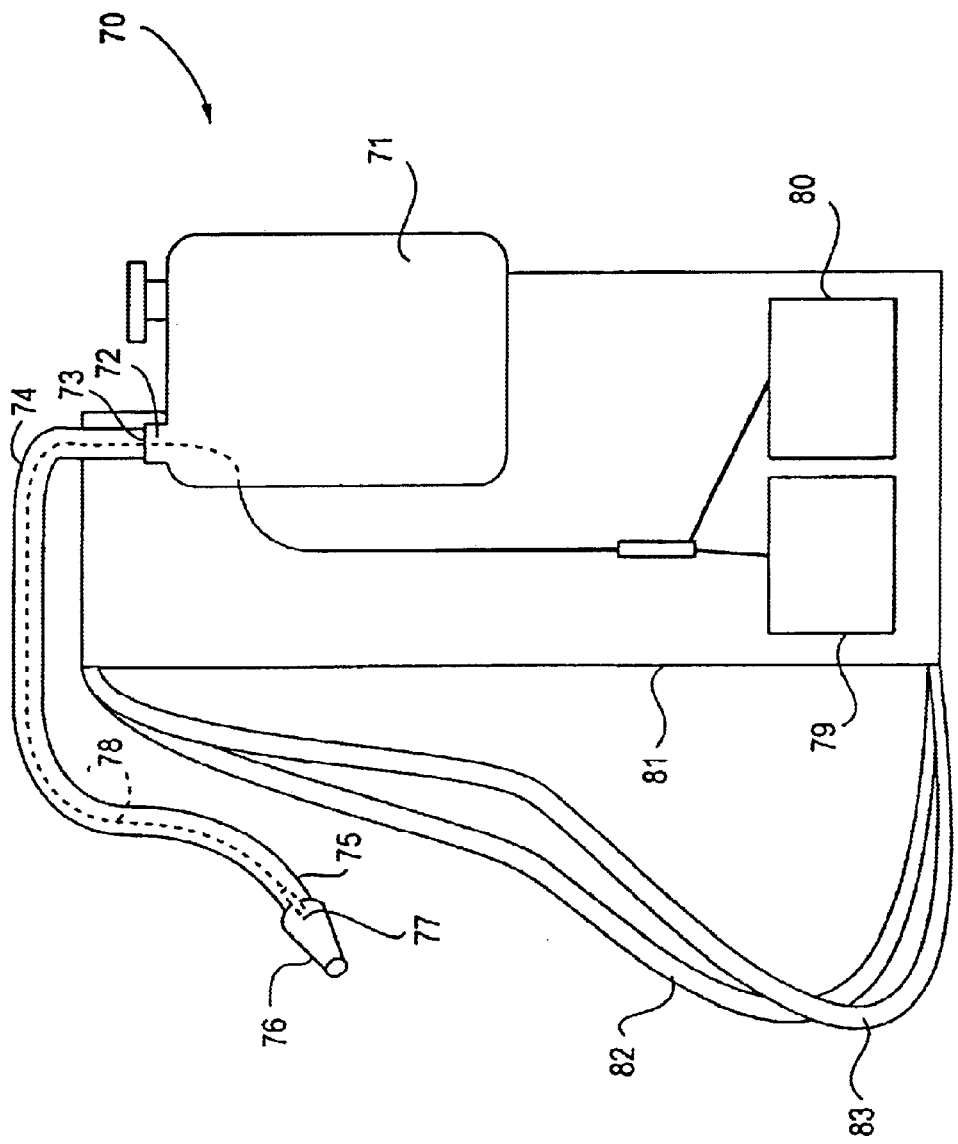
FIG. 7 depicts the structural representation of a portable hydration and sensor device according to certain other preferred embodiments of the present invention.

According to certain particularly preferred embodiments, the present invention provides a portable hydration device comprising a cortisol sensor of the present invention. Applicants have recognized that sensor devices according to the present invention can be used advantageously to provide a portable device capable of being used both to provide hydration to a user and/or to detect levels of cortisol in a fluid sample provided by a user. Referring to FIG. 7, a portable hydration device 70 according to certain embodiments of the present invention comprises a fluid reservoir 71 for storing fluid, the reservoir having an output port 72 onto which the proximal end 73 of a flexible tube, or tube assembly, 74, having a proximal end 73 and a distal end 75, is mounted. Distal end 75 is adapted to provide fluid to a user's mouth. Preferably, as shown in FIG. 7, a mouthpiece 76 is coupled with distal end 75 of assembly 74 such that the mouthpiece is in fluid communication with tube assembly 74 and reservoir 71. In certain embodiments, the mouthpiece may simply comprise the end of tube assembly 75 or may comprise another mouthpiece as described hereinabove. Mouthpiece 76 may be removable from distal end 75 or may be integrated with tube assembly 74.

The portable hydration devices of the present invention further comprise an MIP which is operatively associated with a light source and a detector according to the present invention and which is in fluid communication with both the reservoir and distal end of the tube assembly. By placing the MIP in fluid communication with both the reservoir and distal end, a fluid sample introduced through the distal end is capable of contacting the MIP such that cortisol molecules contained therein are bound to the MIP and detected. In addition, after detection, fluid from the reservoir can be passed over the MIP to flush cortisol molecules from the MIP to regenerate the MIP in preparation for the introduction of a new sample. Typically, the MIP may be located in either a tube assembly or alongside a mouthpiece of the hydration device, when a separate mouthpiece is present. Preferably, a hydration device of the present invention comprises an MIP disposed located alongside a mouthpiece. For example, FIG. 7 shows a hydration device comprising an MIP 77 which is disposed alongside mouthpiece 76 and on the end of optical fiber 78, through which the MIP is operatively associated with a light source 79 and detector 80.

While the exemplary device shown in FIG. 7 shows a single housing, or pack, 81 for the reservoir, detector and light source only, any suitable combination of one or more of the light source, detector, reservoir, and/or portion thereof can be housed within one or more device housings according to the present invention. In addition, while the exemplary device shown in FIG. 7 illustrates one arrangement for the MIP, optical fibers, light source, detector, receptacle and reservoir of the present invention, those of skill in the art will appreciate that any of a wide variety of alternate arrangements are suitable to provide a hydration/cortisol sensor device according to the present invention. For example, the light source, detector and optical fiber(s) through which the light source and detector are optically associated with the MIP, and portions thereof, may be individually positioned alongside mouthpiece 76, tube assembly 74, reservoir 71 and/or housing 81. Reservoir 71, and/or any portion thereof may be within or outside housing 81. In light of the teachings herein, those of skill in the art will be readily able to assemble a hydration/sensor device of the present invention for any of a wide range of applications without undue experimentation.

In preferred embodiments, the portable hydration device according to the present invention is adapted to be worn on a user's body. Accordingly, in such embodiments, any combination of reservoir, tube assembly, mouthpiece, MIP, light source, and detector components may be housed in a pack comprising at least one strap, such as a shoulder or waist strap, for mounting the pack onto the back, chest, and/or waist of a user. For example, the embodiment illustrated in FIG. 7 comprises a pack 81 having two shoulder straps 82 and 83.

Any of a wide range of hydration systems may be adapted for use as a portable hydration device of present invention. For example, a sensor device of the present invention may be incorporated into the hydration devices described, for example, in U.S. Pat. Nos. 5,727,714, 5,060,833, 5,085,349, 6,497,348, which are incorporated in their entirety herein by reference, to provide hydration/sensor device according to the present invention.

Methods

The present invention further provides methods for detecting a cortisol molecule in a fluid sample by: providing a fluid sample comprising a cortisol molecule; contacting the fluid sample with the MIP of a sensor device according to the present invention to chemically bind the cortisol molecule to the MIP; and detecting the cortisol molecule.

Any suitable method for providing a fluid sample comprising at least one cortisol molecule can be used according to the present invention. For example, the provided sample may be prepared by mixing and/or dissolving cortisol into a fluid to prepare a fluid sample. Alternatively, the fluid sample for use herein may be provided by generating or removing a fluid from the human body. For example, a fluid sample comprising saliva as a fluid medium may be provided via salivation and/or expectoration, while a urine sample may be provided for testing via urination and/or catheterization. A blood sample may also be removed and provided according to the present invention. In certain preferred embodiments, a fluid sample is provided according to the present invention via salivation, expectoration, urination, or combinations of two or more thereof.

The provided sample may be contacted with an MIP of the present invention via any suitable method such that at least one cortisol molecule in the sample is capable of binding to the MIP and being detected by a detector. In certain preferred embodiments, the sample is expectorated or urinated directly onto an MIP or into a receptacle in fluid communication with an MIP of the present invention, through which the sample flows to and contacts the MIP.

Any suitable means for detecting the cortisol molecule(s) bound to an MIP can be used in the methods of the present invention. In preferred embodiments, the cortisol molecule(s) are detected via fluorescence detection technology, as described above.

Preferably, the present methods comprise detecting one or more cortisol molecules in a fluid sample in real-time. As noted above, the present invention advantageously reduces the time required between providing a sample and detecting the levels of cortisol therein relative to conventional methods. Accordingly, such methods can be used, for example, by soldiers in field conditions, to continuously measure and update the cortisol levels in the user's body. In light of the teachings herein those of skill in the art will be readily able to detect levels of cortisol in a fluid sample in real-time according to the present methods without undue experimentation.

The devices and methods described herein are useful not only to detect cortisol levels in bodily fluids, but also, may be used in the lab or in the field to detect cortisol levels in any of a wide range of natural or prepared cortisol-containing fluids and products for a wide range of applications. For example, the present devices and methods are suitable for use in quality control of cortisol-containing products, in vitro cortisol assays, and the like.

EXAMPLES

The following examples are illustrative of the present invention and are not intended to be limiting in any manner.

Example 1

This example illustrates the synthesis of 4-vinylbenzaldehyde (suitable for use in the synthesis of 5-(4-boronopthaloyl-amidophenyl)-10,15,20-(4-ethenylphenyl)$_3$-porphyrinato copper(II) via the scheme shown in FIG. 8).

A few crystals of 2,6-di-tert-butyl-4-methylphenol (BHT), 4-Bromobenzaldehyde (2.00 g, 10.8 mmol), and tetrakis(triphenylphosphine) palladium(0) (250 mg, 2 mol %) are dissolved in toluene (20 mL). Tri-n-butyl-vinyl tin(IV) (3.47 mL, 3.77 g, 11.9 mmol) is added and the mixture is heated to reflux for 3 hr. After cooling to room temperature, the dark green/black reaction mixture is treated as follows: pyridine (4.4 mL) is added, then 9.3 mL of pyridinium hydrofluoride in tetrahydrofuran (~1.2N, made by adding 0.88 g of pyridinium polyhydrofluoride into 20 mL dry THF containing 3.13 g of pyridine); the mixture is then stirred at room temperature overnight. The treated reaction mixture is diluted with diethyl ether (200 mL), washed with water (50 mL), 10% aqueous hydrochloric acid (2×50 mL), saturated aqueous NaHCO$_3$ (50 mL), and then dried over MgSO$_4$. Concentration in vacuo gives a crude oil, which is purified by flash chromatography (silica, 10% ethyl acetate/hexanes) to give pure 4-vinylbenzaldehyde as a pale yellow oil (1.16 g, 81.3%).

Example 2

This example illustrates the synthesis of 4-boronophthalidylamido-benzaldehyde suitable for use in the synthesis of 5-(4-boronopthaloyl-amidophenyl)-10,15, 20-(4-ethenylphenyl)$_3$-porphyrinato copper(II) (via the scheme shown in FIG. 8).

The following reaction scheme is used to synthesize 4-boronophthalidylamido-benzaldehyde:

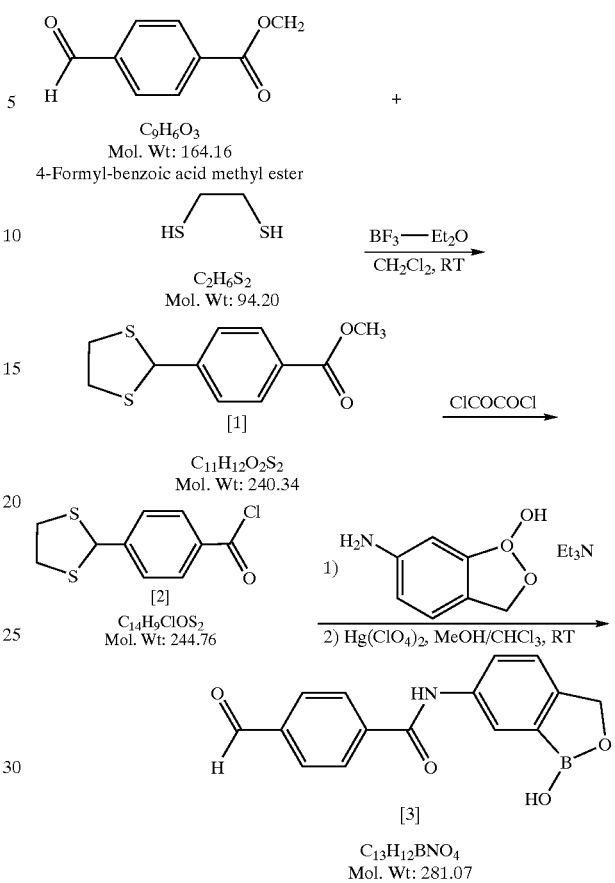

4-Methoxycarbonyl-phenyl-1,3-dithiane [1]. A 250-mL, round-bottomed flask is charged with samples of methyl 4-formylbenzoate (2.6 g, 15.8 mmol), 1,2-ethanedithiol (2.23, 23.7 mmol), and 114 mL of distilled CH$_2$Cl$_2$. Boron trifluoride etherate (0.7 mL, 0.006 mol) is added and the solution is stirred overnight at room temperature. The solution is then poured into a separatory funnel and washed with 30–50 mL of 5% aqueous NaOH. The organic layer is washed with water, dried (Na$_2$SO$_4$), and concentrated to yield a pale yellow oil.

Dithiane-protected benzoyl chloride [2]. Ester [1] (1.00 g, 4.16 mmol) is dissolved in THF (5 mL) and treated with excess oxalyl chloride (3.6 mL, 41.6 mmol). Volatiles are removed in vacuo and the resulting acid chloride is used in the following step without purification.

4-Boronophthalidylamido-benzaldehyde [3]. Acid chloride [2] (1.00 g, 4.09 mmol) is dissolved in THF (5 mL), chilled to 0° C., and treated with a solution of 5-aminoboronophthalide (608 mg, 4.09 mmol) in THF (1 mL), dropwise. Triethylamine (570 µL, 4.09 mmol) is added to absorb the resulting acid and the reaction is allowed to warm to room temperature overnight. Dilution with water (25 mL), followed by extraction with ethyl acetate (3×50 mL) and drying over Na$_2$SO$_4$ gives the crude aldehyde as a yellow solid. Purification by flash chromatography (silica, 10% EtOAc/hexanes) gives pure product. Deprotection of the aldehyde is affected by treatment with Hg(ClO$_4$)$_2$ in methanol and chloroform, at room temperature according to the methodology of Fugita et al. (*Chem. Pharm. Bull.*, 1978, 26, 3743).

5-Aminoboronophthalide. Boronophthalide (2.86 g, 21.4 mmol) is added to 18.6 mL of chilled, fuming nitric acid (at 45° C.) in portions over 4 minutes with stirring. The reaction is quenched with ice and water (40 g and 60 mL), then the resulting pale yellow solid is collected on a Büchner filter and washed with 75 mL of water. Drying the solid in vacuo over $P_2O_5$ gives 2.72 g (15.2 mmol, 71.0%) 5-Nitroboronophthalide as a pale yellow solid (m.p. 178–179° C.).

5-Nitroboronophthalide (2.72 g, 15.2 mmol) and 10% palladium on carbon (911 mg) are suspended in 30 mL of anhydrous tetrahydrofuran. Ammonium formate (4.41 g, 70 mmol) is added and the mixture is stirred at 50° C., under nitrogen for 3 hr. After cooling to room temperature, the catalyst is removed by filtration through a pad of Celite, which is then washed with ~30 mL of methanol. Concentration in vacuo gives a light brown oil that is purified by dissolution in ethyl acetate and filtration through a plug of silica. Recrystallization from ethanol and water gives a light yellow crystalline solid (1.12 g, 7.52 mmol, 49.5%) with a m.p. of 160–161° C.

Example 3

This example illustrates the synthesis of a substituted porphyrin chromophore according to certain embodiments of the present invention.

4-Boronophthalidylamido-benzaldehyde (35.1 mg, 0.125 mmol), 4-vinylbenzaldehyde (49.6 mg, 0.375 mmol), and pyrrole (34.8 µL, 0.5 mmol) are dissolved in 50 mL of dry chloroform and purged with nitrogen. The reaction is catalyzed with $BF_3$ etherate (10 µL of a 2.5M solution in $CH_2Cl_2$) and then stirred at room temperature for 60 minutes to form the intermediate porphyrinogen. This intermediate is then oxidized by addition of p-chloranil (92.0 mg, 0.375 mmol) and the flask is immersed in a water bath preheated to 45° C. After a 1 hr reflux, the solution is poured into a 250-mL, round-bottomed flask containing 10 g of Florisil and the resulting slurry is evaporated to dryness. The powder is poured on top of a silica column. The desired product was isolated by flash chromatography with $CH_2Cl_2$/petroleum ether (9:1).

What is claimed is:

1. A sensor device for detecting cortisol molecules, said device comprising a molecularly imprinted polymer comprising a cortisol-binding chromophore that fluoresces upon excitation operatively associated with:
   a source of excitation energy for said chromophore; and
   a detector for detecting fluorescent energy emitted upon chromophore excitation; wherein an excited cortisol-binding chromophore that does not have a cortisol molecule associated therewith fluoresces differently than an excited cortisol-binding chromophore that does have a cortisol molecule associated therewith.

2. The sensor device of claim 1 wherein said chromophore comprises a porphyrin.

3. The sensor device of claim 2 wherein said chromophore is 5-(4-boronopthaloyl-amidophenyl)-10, 15, 20-(ethenylphenyl)$_3$-porphyrinato copper (II).

4. The sensor device of claim 1 wherein said source of excitation energy is selected from the group consisting of an argon laser, blue laser, tunable laser, light emitting diode, and combinations of two or more thereof.

5. The sensor device of claim 4 wherein the detector is selected from the group consisting of a spectrophotometer, spectrometer, photomultiplier tube, CCD camera equipped with a monochromator, filters, the naked eye, and combinations of two or more thereof.

6. The sensor device of claim 1 further comprising at least one optical fiber, having a proximal end and a distal end, for transmitting light energy, wherein said molecularly imprinted polymer is disposed on the distal end of the optical fiber, said source of excitation energy is operatively associated with said optical fiber such that said fiber is capable of transmitting excitation energy generated by the source of excitation energy to said molecularly imprinted polymer, and said detector is operatively associated with said optical fiber such that said detector is capable of detecting fluorescence from said chromophore.

7. The sensor device of claim 1 further comprising a fluid receptacle in fluid communication with said molecularly imprinted polymer.

8. The sensor device of claim 7 wherein said fluid receptacle is selected from the group consisting of mouthpieces, cups, bulbs, tubes, bowls, bladders, and combinations of two or more thereof.

9. The sensor device of claim 8 wherein said fluid receptacle comprises a mouthpiece.

10. The sensor device of claim 9 wherein at least a portion of said mouthpiece is formed from said molecularly imprinted polymer.

11. The sensor device of claim 9 wherein at least a portion of said mouthpiece is coated with said molecularly imprinted polymer.

12. The sensor device of claim 1 further comprising a fluid reservoir in fluid communication with said molecularly imprinted polymer.

13. The sensor device of claim 12 wherein said fluid reservoir comprises a device selected from the group consisting of bladders, bulbs, cups, tanks, tubes, and combinations of two or more thereof.

14. The sensor device of claim 12 wherein said fluid reservoir comprises an input port.

15. A portable hydration device comprising:
   a fluid reservoir capable of holding a hydrating fluid;
   a tube assembly comprising a proximal end and a distal end, said proximal end being coupled to said reservoir and said distal end being adapted to receive hydrating fluid from the reservoir; and
   a sensor device according to claim 1 wherein said molecularly imprinted polymer is in fluid communication with said fluid reservoir and said distal end of said tube assembly.

16. The portable hydration device of claim 15 further comprising a mouthpiece coupled with said distal end of said tube assembly.

17. The portable hydration device of claim 16 comprising a portable pack capable of receiving at least a portion of one or more of the devices selected from the group consisting of said reservoir, tube assembly, mouthpiece, molecularly imprinted polymer, light source, detector, and combinations of two or more thereof.

18. The portable hydration device of claim 17 further comprising at least one strap for mounting said pack onto a user.

19. A method of detecting a cortisol molecule comprising:
   providing a fluid sample comprising at least one cortisol molecule; and
   contacting the fluid sample with the molecularly imprinted polymer of a sensor device of claim 1 to associate the cortisol molecule with the molecularly imprinted polymer; and
   detecting the cortisol molecule.

20. The method of claim 19 wherein said providing step comprises providing a saliva-based sample via expectoration or salivation.

21. The method of claim 19 wherein said providing step comprises providing a urine-based sample via urination.

22. The method of claim 19 wherein said cortisol molecule is detected in real-time.

* * * * *